(12) United States Patent
Chmii et al.

(10) Patent No.: US 6,184,540 B1
(45) Date of Patent: Feb. 6, 2001

(54) METHOD OF PREPARING A THIOPHENE-CONTAINING OR FURAN-CONTAINING CONJUGATED COMPOUND AND PRECURSOR COMPOUND AND USE THEREOF FOR MAKING SEMICONDUCTOR DEVICE

(75) Inventors: Knut H. Chmii; Adam R. Brown; Dagobert M. De Leeuw, all of Eindhoven; Edsko E. Havinga, Waalre; Anita Pomp, Eindhoven; Wolter Ten Hoeve, Eelde; Hans Wijnberg, Groningen, all of (NL)

(73) Assignee: U.S. Philips Corporation, New York, NY (US)

( * ) Notice: Under 35 U.S.C. 154(b), the term of this patent shall be extended for 0 days.

(21) Appl. No.: 09/249,968

(22) Filed: Feb. 12, 1999

Related U.S. Application Data (62) Division of application No. 09/158,630, filed on Sep. 22, 1998, now Pat. No. 5,919,951, which is a division of application No. 09/039,599, filed on Mar. 16, 1998, now Pat. No. 6,124,475.

(30) Foreign Application Priority Data

Mar. 14, 1997 (EP) .................................................. 97200760

(51) Int. Cl.$^7$ ....................... C07D 407/14; C07D 409/14
(52) U.S. Cl. ............................... 257/40; 428/419; 549/60; 549/59
(58) Field of Search ............................. 257/40; 428/419; 549/59, 60

(56) References Cited

PUBLICATIONS

"Highly Conducting, Poly(2,5–Thienylene Vinylene) Prepared Via A Soluble Precursor Polymer" Jen Et Al, J. Chem. Soc. Chem. Comm. 1987 P. 309–311.

"The Palladium–Catlyzed Cross–Coupling Reactions of Organotin Reagents With Organic Electrophiles" J. Stille, Angew. Chem. Int. Ed. England 1986. P. 508–524.

"A Simple Two–Step Synthesis Of A Novel, Fully Aromatic Ladder–Type Polymer" K. Chmil Et Al, Makromol. Chem Rapid Comm. 1993, 14, P.217–222.

"Novel Approaches Toward Ninhydrin Analogs" R. Hark Et Al, Tetrahedron Letters, vol. 35, No. 42, pp. 7719–7722, 1994.

"Synthesis And Properties Of 2–or 2,5 Substituted Thiophene And 2–Or 2,5'Substituted Dithiophene Derivatives Of Platinum" S. Kotani Et Al, Jour. Of Organometallic Chemistry, 429 (1992) P. 403–413.

*Primary Examiner*—Joseph K. McKane
*Assistant Examiner*—Taofiq A. Solola
(74) *Attorney, Agent, or Firm*—Ernestine C. Bartlett (57) ABSTRACT

The invention relates to a method of preparing thiophene-containing or furan-containing conjugated compounds such as polythiophene. The method uses a precursor compound having tetrahydrothiophene or tetrahydrofuran precursor units having arylthio or alkylthio substituents. The precursor units can be thermally converted into thiophene or furan units. Due to the presence of the precursor units the precursor compound is soluble and can, unlike the corresponding conjugated compound, be processed from solution.

20 Claims, 1 Drawing Sheet

METHOD OF PREPARING A THIOPHENE-CONTAINING OR FURAN-CONTAINING CONJUGATED COMPOUND AND PRECURSOR COMPOUND AND USE THEREOF FOR MAKING SEMICONDUCTOR DEVICE

CROSS REFERENCE TO RELATED APPLICATIONS

This is a divisional of application Ser. No. 09/158,630, filed Sep. 22, 1998, now U.S. Pat. No. 5,919,951 which is a divisional of application Ser. No. 09/039,599, now U.S. Pat. No. 6,124,475 filed Mar. 16, 1998.

FIELD OF THE INVENTION

The invention relates to a method of preparing a thiophene-containing or furan-containing conjugated compound, whereby a soluble precursor compound, comprising a precursor unit having thermally separable substituents, is heated such that said thermally separable substituents are eliminated from said precursor compound while converting said precursor compound into said thiophene-containing or furan-containing conjugated compound. The invention also relates to precursor compounds suitable for use in such a method. The invention further relates to a semiconductor device in which use is made of a conjugated compound obtainable by using such a method.

BACKGROUND OF THE INVENTION

Conjugated compounds, or more in particular, thiophene-containing or furan-containing conjugated compounds are used in various industrial applications. For example, they can be used as dyes or pigments, as (semi)conductors, (electro)luminescent material or in electr(on)ical, optical and electro-optical devices such as light emitting diodes, field-effect transistors, solar cells, polarizing optical elements and batteries. In the context of the invention a compound is considered to be conjugated if, upon electronic excitation, it absorbs ultraviolet light or radiation of lower frequencies.

However, due to the inherent rigidity of the conjugated system, many potentially interesting conjugated compounds are insoluble. For many industrial applications processability from solution and therefore solubility is an essential requirement if an economically viable process is to be obtained.

To enhance the solubility of a conjugated compound it has been proposed to include solubilizing substituents such as large alkyl or alkoxy groups. However, this has the undesired side-effect that properties other than the solubility, such as the charge-carrier mobility, are adversely affected as well.

In order to enhance the processability from solution, it has also been proposed to use a method of the type mentioned in the opening paragraph. In such a method, referred to as a precursor method for short, the processing, such as, for example, the formation of a layer by spincoating, is done using the precursor compound. As a final step, the precursor compound is (thermally) converted by separating the separable substituents from the remainder of the compound thus forming the conjugated compound. Only a few conjugated compounds have been prepared by a method which uses such precursor compounds. One example is poly(2,5-thienylenevinylene) as disclosed in a publication by Kwan-Yue Jen et al. in J. Chem. Soc., Chem. Comm., 1987, p309. Since the precursor method is a very attractive method of rendering conjugated compounds processable from solution, there still exists a need for methods of preparing a conjugated compound using precursor compounds.

SUMMARY OF THE INVENTION

It is an object of the invention to provide, inter alia, a method of preparing a thiophene-containing or furan-containing conjugated compound from a precursor compound which is processable from solution and thermally convertible to said thiophene-containing or furan-containing conjugated compound.

The object of the invention is achieved by a method of the type mentioned in the opening paragraph which, according to the invention, is characterized in that the precursor unit used is a tetrahydrothiophene or tetrahydrofuran unit having thermally separable substituents —$SR_1$ and —$SR_2$, wherein $R_1$ and $R_2$ are independently selected as an all or aryl group. In the method according to the invention use is made of thermally convertible precursor compounds having precursor units which, after elimination of the thermally separable substituents by heating to an adequate temperature of, typically 200° C., are converted into thiophene or furan heterocycles. The presence of the precursor units enhances the solubility of the precursor compound of which they are part relative to the conjugated compound which contains the corresponding thiophene or furan units. The precursor units can be suitably used in any method of preparing a thiophene or furan-containing compound but preferably they are used to prepare conjugated compounds. Precursor units which can be converted into thiophene or furan units were hitherto unavailable and allow conjugated compounds which are known to be rather intractable, such as unsubstituted polythiophene, to be processed as though they are soluble.

The improved processability is most advantageously exploited in conjunction with a substrate. A preferred embodiment of the method according the invention is therefore characterized in that, before the precursor compound is heated, a solution comprising the precursor compound is prepared and provided onto a substrate. Suitably, the substrate is made, for example, of glass, quartz, silicon or a synthetic resin. The conjugated compound can be processed in the form of a layer by any conventional method which uses a solvent, for example, by spincoating a solution of the precursor compound onto the substrate.

Heating is suitably performed by conventional means such as an oven or a hot plate. Though not essential, heating may be performed under reduced pressure or under an inert atmosphere.

The precursor compound used in the method according to the invention contains precursor units derived from the heterocycles tetrahydrothiophene or tetrahydrofuran. Since in most thiophene-containing or furan-containing compounds the thiophene or furan ring is substituted at both the 2 and 5 position, use is made in particular of precursor units which are substituted correspondingly by non-separable substituents.

In addition to said substituents, the precursor unit has thermally separable substituents. By heating or, depending on the type of separable substituent, any other suitable method such as irradiation, these substituents are separated from the precursor unit. The separation takes place by way of a β elimination reaction which involves two groups on adjacent atoms, one group of which is the thermally separable group. The reaction produces a double bond on the heterocycle, thus converting the tetrahydrothiophene or tetrahydrofuran into the corresponding dihydro heterocycle.

Two thermally separable substituents suffice to convert a tetrahydrothiophene (tetrahydrofuran) into its thiophene (furan) analog. The first of said two thermally separable substituents can be located at the 2 position, but from a synthetic point of view the 3 position is preferred. Analogously, the second thermally separable substituent is located at the 4 position.

Examples of thermally separable substituents are sulfone, sulfoxide, alkoxy, aryloxy, such as phenoxy, amino, —$NR_3^+$, or —$SR_2^+$ groups. Suitable precursor units are tetrahydrothiophene or tetrahydrofuran units having thermally separable substituents —$SR_1$ and —$SR_2$, wherein $R_1$ and $R_2$ are independently selected as an alkyl or aryl group.

Preferably, a precursor unit is used according to the formula (I)

wherein X is equal to O or S, and $R_1$ and $R_2$ independently selected as an alkyl or aryl group. By heating to a temperature of, typically, 200° C. or higher, the thermally separable groups —$SR_1$ and —$SR_2$ are eliminated thus forming the sulfides $R_5SR_1$ and $R_6SR_2$ and a conjugated unit in the form of a thiophene (X=S) or furan (X=O) unit having substituents $R_3$ and $R_4$ located at the positions 3 and 4 respectively. The substituents $R_3$ and $R_4$ can be varied so as to obtain a range of conjugated compounds which can be rendered processable from solution. Since the tetrahydro unit itself is not conjugated, which has a solubility enhancing effect, and the substituents $R_1$, $R_2$, $R_5$, and $R_6$ enhance the solubility as well, the choice of substituents $R_3$ and $R_4$ is not limited by solubility considerations. Suitable choices are for example methyl, ethyl, (m)ethoxy, nitro or hydrogen.

The substituents $R_1$, $R_2$, $R_5$, and $R_6$ are not part of the conjugated compound which is obtained after thermal conversion and can, for example, be used to influence the temperature at which the thermal conversion occurs or can be chosen so as to obtain a convenient processing or synthetic route. Preferably, they are chosen such that the sulfide to be eliminated vaporizes at the temperature at which the thermal conversion is carried out.

A suitable choice of $R_5$ and $R_6$ is hydrogen. Substituents $R_1$ and $R_2$ are preferably selected from the group consisting of phenyl, 4-methylphenyl, 4-chlorophenyl, 4-nitrophenyl, 4-pyridyl, ethyl and tert-butyl. Surprisingly, the rate and temperature of conversion is almost the same throughout this group. Also, the thermal conversion proceeds faster if the substituents —$SR_1$ and $R_5$ (or —$SR_2$ and $R_6$) are in a trans conformation with respect to each other.

The thermally separable substituent can also be eliminated from the precursor compound by using a base as a catalyst, preferably in solution.

In order to reduce the number of isomers of the precursor compounds which will be formed during synthesis, $R_1$ is preferably chosen equal to $R_2$. Reducing the number of isomers makes the synthetic procedure and in particular the purification of crude products much simpler.

A preferred method according to the invention is characterized in that use is made of a 2,5-dithienyltetrahydrothiophene or 2,5-dithienyltetrahydrofuran unit as the precursor unit. Said precursor units are convenient building blocks in the synthesis of precursor compounds of which use is made in methods according to the invention. For example, the thiophene rings can be selectively brominated at the (unsubstituted) 2 and 5 positions. The (di)bromo compounds thus obtained can be suitably used in a large variety of well known coupling reactions, such as the palladium catalyzed reaction between a bromo compound and an aromatic stannane (see for instance, J. K. Stille, Angew. Chem., Int. Ed. Engl. 1986, 25, p508), or the coupling of two bromo compounds using a nickel-based catalyst (see for instance, K. Chmil et al in Makromol. Chem. Rapid Commun. 1993, 14, p217)

Another preferred embodiment of the method according to the invention is characterized in that the thiophene-containing or furan-containing conjugated compound being prepared is a polymer having a substantially conjugated backbone. In the context of the invention, the term polymer includes oligomer. Processability from solution is a property which many a polymer having a substantially conjugated backbone does not possess. Due to the presence of an extensive conjugated system, in many cases a potentially interesting conjugated polymer compound cannot be synthesized at all or only if it has a low molar mass. The method according to the invention can therefore be applied with particular advantage to such conjugated polymers.

An example of a conjugated polymer which can be rendered soluble by the method according to the invention is a polythiophene. Polythiophenes are semiconductors, can be easily doped and are quite stable. However, the availability of these compounds is hampered by solubility problems. For example, a polythiophene without any substituents is only soluble up to the hexamer. Polythiophene of higher molecular weight can be prepared by electrochemical polymerization but this leads to intractable films as well as to a polythiophene having a backbone which has many topological defects. Using the method according to the invention an unsubstituted polythiophene can be prepared which is substantially free of topological defects and of relatively high molecular weight. A suitable precursor compound uses tetrahydrothiophene precursor units having arylthio or alkylthio groups as the thermally separable substituents. A ratio of one precursor unit to two thiophene units is already sufficient to render the precursor compound soluble in many common organic solvents thus allowing polythiophene films of high quality to be obtained on a variety of substrates.

The polythiophene samples prepared using the method according to the invention are of high molecular weight. Gel permeation chromatographic analysis indicates that a number-average molecular weight of at least 3500 can be routinely obtained. The optical absorption spectrum shows a broad peak between 350 and 750 nm which is characteristic of polythiophene. However, unlike polythiophene samples which are not according to the invention, the broad peak shows various shoulders. This is considered to be due to the absence of topological defects.

The invention further relates to precursor compounds which can be suitably used in a method according to the invention.

A suitable precursor compound is a soluble precursor compound comprising a precursor unit consisting of a tetrahydrothiophene or tetrahydrofuran unit having thermally separable substituents —$SR_1$ and —$SR_2$, wherein $R_1$ and $R_2$ are independently selected as an alkyl or aryl group.

Examples of such suitable precursor compounds have already been described hereinabove. Also suitable are of course intermediate precursor compounds comprising as a precursor unit a dihydrothiophene or dihydrofuran unit which can be obtained from the precursor compounds described hereinabove by heating such that some, but not all, of the thermally separable substituents are eliminated from the precursor compounds thus forming the intermediate precursor compounds.

The intermediate compounds need not be obtained by partial thermal conversion of the tetrahydro heterocycle. For example, treatment of 3,4-bis(phenylthio)-2,5-di(2-thienyl)-tetrahydrothiophene with 2-thienyllithium at −20° C. results in the corresponding dihydro compound, 3-phenylthio-2,5-di(2-thienyl)-2,3-dihydrohydrothiophene. The dihydro compounds have lower conversion temperatures than the corresponding tetrahydro compounds.

The invention also relates to a semiconductor device having a semiconducting layer comprising a polythiophene which is obtainable by using a method according to the invention.

In a preferred embodiment, the semiconductor device is a field-effect transistor in which the semiconducting field-effect active layer comprises unsubstituted polythiophene, where the term polythiophene is understood to include oligothiophene. By determining current voltage characteristics at various gate voltages a pronounced field-effect is observed. A typical value of the field-effect charge-carrier mobility is approximately $10^{-6}$ cm$^2$/(Vs) at a bulk conductivity of $8 \times 10^{-9}$ S/cm. These values are typical of amorphous semiconducting polymers processed from solution. A good field-effect transistor combines a high mobility with a low bulk conductivity.

BRIEF DESCRIPTION OF THE DRAWINGS

The invention will be further elucidated with the aid of the following examples.

In the drawings.

DETAILED DESCRIPTION OF THE PREFERRED EMBODIMENTS

Example 1

Synthesis of 3,4-bis(phenylthio)-2,5-di(2-thienyl)-tetrahydrofuran 2-phenylthioacetic acid Thiophenol (521 g, 4.736 mol) in 800 ml THF is added to a cold mixture of sodium hydroxide (400 g, 10 mol) and 2 kg ice. Sodium bromide (50 g) and triethylbenzylammonium chloride (8 g) are added to the 20° C. mixture which is stirred mechanically in a large beaker. Chloroacetic acid (500 g, 5.29 mol) is added portionwise at a temperature of 30–40° C. and at the same time ice is being added in order to moderate the exothermal reaction. At the end of the chloroacetic acid addition another 80 g sodium hydroxide is added to make the mixture basic. The thick paste is diluted with so much water that a stirrable paste is obtained (the total volume being about 7 l). After stirring for 2 hours and standing overnight, the paste is acidified with concentrated hydrochloric acid. Air is bubbled through the mixture in order to remove the THF and allow the product to crystallize. It is collected by filtration and washed with water. After air-drying there is obtained 762 g (4.536 mol, 96%) of 2-phenylthioacetic acid.

2-phenylthioacetyl chloride

A quantity of 762 g (4.536 mol) of 2-phenylthioacetic acid is stirred at room temperature for 3 hours with thionyl chloride (375 ml, 5.14 mol), then stirred at 40° C. for 3 hours. Rotary evaporation followed by bulb-to-bulb distillation gives 777 g (4.166 mol, 92%) of 2-phenylthioacetyl chloride.

2-phenylthio-1-(2-thienyl)-ethanone

To a cooled mixture of 2-phenylthioacetyl chloride (593 g, 3.18 mol), thiophene (286 g, 3.40 mol), and 1500 ml toluene, tin(IV)chloride (875 g, 3.36 mol) is added over a period of 2 to 3 hours at temperatures between 0 and 7° C. The mixture is then stirred for 3 hours whereby the temperature of the reaction mixture rises gradually to room temperature. Some ice is added carefully to the mixture followed by 100 ml concentrated hydrochloric acid in 1500 ml water. The layers are separated and the organic layer is washed with 2×500 ml water. The aqueous layers are extracted with 1 l toluene. The organic layers are dried and rotary evaporated. The residue is stirred with 1500 ml methanol, then filtered, the solid being washed with 1 l methanol. A quantity of 421 g of 2-phenylthio-1-(2-thienyl)-ethanone is obtained. The filtrate is rotary evaporated and the residue is purified by bulb-to-bulb distillation. The product, which distils at about 140° C. and 1 mm Hg, is stirred with methanol to give a pure product. The filtrate of this crystallization is rotary evaporated and the residue is allowed to stand with some seed crystals. The supernatant liquid is poured off and the residue is stirred with methanol to give an additional amount of product. The total yield is 627 g (2.68 mol, 84%).

$^1$H NMR (CCl$_4$): δ4.0 (s, 2H), 6.9–7.6 (m, 8H).

2,3-bis(phenylthio)-1,4-di(2-thienyl)-1,4-butanedione 2-phenylthio-1-(2-thienyl)-ethanone (231.4 g, 0.989 mol) is added at −3 to 3° C. in portions over a period of 1.5 hours to a mixture of sodium hydride (37.5 g, 55–65% dispersion in oil, 1.016 mol maximum) and 950 ml THF. After stirring for 30 min at −5° C., the solution is cooled and cupric chloride (120 g, 0.893 mol) is added at −72° C. The mixture is allowed to warm up slowly with mechanical stirring (after 3 hours the internal temperature is −10° C. and after 5 hours 5° C.). It is subsequently stirred for 4 hours at 10 to 20° C. before it is heated at. 43° C. for 11 hours. After rotary evaporation (the THF can be reused) 500 ml 2 N hydrochloric acid and 1500 ml toluene are added to the residue. The mixture is stirred, then filtered under vacuum and the layers are separated. The organic layer is washed with 2×150 ml water, then dried and evaporated to leave about 120 g residue. The solid is stirred at 50° C. with 1500 ml toluene and the first aqueous layer. Filtration, separation, washing with the other water layers, drying and evaporation gives another 30 g. These combined product fractions contain some starting material. The solid is boiled with 750 ml chloroform, the mixture is filtered while hot over a big plug of cotton wool and the filtrate is rotary evaporated. The undissolved material is boiled once more with 500 ml chloroform, the mixture is filtered while hot over a plug of cotton wool and the filtrate is rotary evaporated. To the combined filtrates, which contain both the meso and dl isomer of 2,3-bis(phenylthio)-1,4-di(2-thienyl)- 1,4-butanedione, 600 ml toluene and 3.6 g diethylamine are added and the mixture is stirred for 20 hours at room temperature. Filtration and washing with toluene gives 137 g of the pure meso isomer(0.294 mol. 59%). The filtrate is rotary evaporated and the residue is purified by bulb-to-bulb distillation. The distillate fraction, which boils at 140° C. and 1 mm Hg is stirred with methanol. This gives 24 g of the starting compound.

$^1$H NMR of the dl-isomer (CDCl$_3$): δ4.65 (s, 2H), 7.0–7.6 (m, 16H).

$^1$H NMR of the meso-isomer (CDCl$_3$): δ4.85 (s, 2H), 7.1–7.8 (m, 16H).

2,3-bis(phenylthio)-1,4-di(2-thienyl)-1,4-butanediol

A mixture of lithium aluminum hydride (30.8 g, 0.789 mol) and 1 l THF is cooled with liquid nitrogen to about −10° C. Meso 2,3-bis(phenylthio)-1,4-di-(2-thienyl)-1,4-butanedione (288.88 g, 0.620 mol) is added in portions over a period of 30 minutes at temperatures between 0 and −10° C. After the addition the mixture is stirred mechanically for 20 minutes at the same temperature. Ethylacetate (200 ml) is added dropwise while cooling well at temperatures below 7° C., followed by 200 ml acetic acid at the same temperatures. The mixture is stirred for 5 minutes, then poured in 800 ml 4 N hydrochloric acid. The layers are separated and the organic layer is washed with 2×250 ml brine, then dried and rotary evaporated. The aqueous layers are extracted with 1 l ethylacetate, which is dried and combined with the partially evaporated THF-layer. Rotary evaporation is continued until about 500 g residue is left. About 300 ml methanol is added to this suspension, stirring, filtration and washing with methanol gives 248.72 g of 2,3-bis(phenylthio)-1,4-di(2-thienyl)-1,4-butanediol. The filtrate is rotary evaporated and the residue is stirred with some methanol to give another 8.50 g of the same compound, resulting in a total yield of 257.22 g (0.547 mol. 88%).

$^1$H NMR (CDCl$_3$): δ2.7 (bs, 2H, exchange with D$_2$O), 3.6 (bs, 2H), 5.7 (bs, 2H), 6.8–7.2 (m, 16H).

3,4-bis(phenylthio)-2,5-di(2-thienyl)-tetrahydrofuran

To a suspension of 2,3-bis(phenylthio)-1,4-di(2-thienyl)-1,4-butanediol (54.0 g, 114.9 mmol) in 350 ml dioxane there is added 8.70 g conc. sulfuric acid in 4 almost equal portions with a 45 minutes interval between each addition. The rather thick suspension is stirred mechanically for 4 days at room temperature whereby a clear solution is obtained. The solution is poured into 500 ml water and the product is extracted with 2×300 ml toluene. The organic layer is washed with 2×250 ml water, then dried and rotary evaporated. A quantity of 50 ml ether, followed by 200 ml methanol as well as some seed crystals are stirred into the residue. The crystallized product is filtered off and washed with methanol. It weighs 21.83 g. The filtrate is rotary evaporated and the residue is chromatographed on an aluminum oxide column (16×3 cm) using a 1/1 mixture of toluene and hexane as the eluent, thus obtaining a fraction with an additional amount of the product. This fraction is rotary evaporated and the residue is dissolved in some ether. Methanol is added while stirring, whereupon 3,4-bis(phenylthio)-2,5-di(2-thienyl)-tetrahydrofuran crystallizes. It is isolated in the usual way and weighs 7.04 g. The total yield is 28.87 g (63.9 mmol, 56%).

$^1$H NMR (CDCl$_3$): δ4.2–4.4 (m, 2H), 5.5 (d, 1H), 5.9 (d, 1H), 6.9–7.4 (m, 16H).

The product, 3,4-bis(phenylthio)-2,5-di(2-thienyl)-tetrahydrofuran, is a precursor compound having a precursor according to the formula (I) wherein X=O, R$_1$=R$_2$=Ph, R$_3$=R$_4$=R$_5$=R$_6$=H, which can be suitably used in a method according to the invention. Heating the compound to approximately 250° C. for 30 minutes yields the conjugated compound 2,5-di(2-thienyl)-furan.

Example 2

Synthesis of 3,4-bisphenylthio-2,5-di(2-thienyl)-tetrahydrothiophene

Lawesson's reagent (151.6 g, 0.375 mol) is stirred with 1 l pyridine at 50° C. for 1 hours, resulting in a solution, and 2,3-bis(phenylthio)-1,4-di(2-thienyl)-1,4-butanediol as obtained in Example 1 (129.52 g, 0.276 mol) is added and the mixture is stirred for 1 hours at 50–60° C., resulting in a rather thick suspension. The suspension is warmed up to 90° C. over a period of 2 hours and then kept at 90±3° C. for 3 days (becoming a clear solution after 2 days). The solution is rotary evaporated (the solvent is used for similar reactions) and the residue is stirred for 30 minute with 1 l toluene and 750 ml 2 N sodium hydroxide solution. The layers are separated and the organic layer is washed with 2×300 ml water. The aqueous layers are extracted with 500 ml toluene. The organic layers are dried and rotary evaporated. The residue is stirred with hexane to which so much toluene is added that the oil is converted into a crystalline solid. Filtration and washing gives the crude unsymmetrical isomer which is combined with 15.0 g of a similar crude product and then purified over a short aluminum oxide column using hexane/toluene (1/1) as the eluent. The eluent is rotary evaporated and the residue is recrystallized from toluene/hexane to yield 55.46 g of the unsymmetrical isomer of 3,4-bis(phenylthio)-2,5-di(2-thienyl)-tetrahydrothiophene. The filtrates from both crystallizations are combined and filtered over an aluminum oxide column (together with some other filtrates from two similar reactions). The elution is carried out using hexane containing increasing amounts of toluene. Several fractions are obtained. The first fractions contain an impurity, which probably results from dehydration of the diol. The next fractions with mainly the symmetrical isomer are combined, rotary evaporated and the residue is recrystallized from hexane/toluene. The next column fractions are a mixture of the symmetrical and unsymmetrical isomer. The next column fractions, which are enriched in the unsymmetrical isomer, are combined and rotary evaporated, and the residue is recrystallized from hexane/toluene to give the unsymmetrical isomer. The filtrates of the crystallizations and the mixed fractions are combined and again purified over an aluminum oxide column. Further purification then gives an additional amount of the symmetrical and unsymmetrical isomer. A total amount of 108.01 g of the symmetrical and unsymmetrical isomer is thus obtained from 3 reactions starting from a total of 248.02 g of 2,3-bis(phenylthio)-1,4-di(2-thienyl)-1,4-butanediol (0.231 mol, 44%).

$_1$H NMR (CDCl$_3$) of the unsymmetrical isomer: δ4.0–4.2 (m, 2H), 5.1 (d, J=10 Hz, 1H), 5.55 (d, J=4 Hz, 1H), 6.8–7.3 (m, 16H).

$^1$H NMR (CDCl$_3$) of the symmetrical isomer: δ4.2 (d, J=5 Hz, 2H), 5.0 (d, J=5 Hz, 2H), 6.8–7.4 (m, 16H).

The product, 3,4-bisphenylthio)-2,5-di(2-thienyl)-tetrahydrothiophene, is a precursor compound having a precursor unit according to the formula (I) wherein X=S, R$_1$=R$_2$=Ph, R$_3$=R$_4$=R$_5$=R$_6$=H, which can be suitably used in a method according to the invention. When heated at 175° C. for 30 min, thiophenol is quantitatively eliminated and the conjugated compound terthiophene is obtained.

Example 3

Synthesis of 3,4-bis((4-chloro)phenylthio)-2,5-di(2-thienyl)-tetrahydrothiophene

Starting from 4-chlorothiophenol, the synthesis of this compound is analogous to that of the tetrahydrothiophene synthesized in Example 2.

$^1$H NMR (CDCl$_3$): δ3.9–4.1 (m, 2H), 5.05 (d, J=10 Hz, 1H), 5.55 (d, J=4 Hz, 1H), 6.8–7.3 (m, 14H).

The product, 3,4-bis[(4-chloro)phenylthio]-2,5-di(2-thienyl)-tetrahydrothiophene, is a precursor compound having a precursor unit according to the formula (I), wherein X=S, R$_1$=R$_2$=4-chlorophenyl, R$_3$=R$_4$=R$_5$=R$_6$=H, which can be suitably used in a method according to the invention. When heated at 175° C. for 30 minutes, 4-chlorothiophenol is quantitatively eliminated and the conjugated compound terthiophene is obtained.

Example 4

Synthesis of 3,4-bis((4-methyl)phenylthio)-2,5-di(2-thienyl)-tetrahydrothiophene Starting from thiocresol, the synthesis of this compound is analogous to that of the tetrahydrothiophene synthesized in Example 2.

$^1$H NMR (CDCl$_3$): δ2.25 (ss, 6H), 3.9–4.1 (m, 2H), 5.05 (d, J=10 Hz, 1H), 5.5 (d, J=4 Hz, 1H), 6.9–7.3 (m ,14H).

The product, 3,4-bis(4-methyl)phenylthio-2,5-di(2-thienyl)-tetrahydrothiophene, is a precursor compound having a precursor unit according to the formula (I), wherein X=S, R$_1$=R$_2$=4-methylphenyl, R$_3$=R$_4$=R$_5$=R$_6$=H, which can be suitably used in a method according to the invention. When heated at 175° C. for 30 minutes, 4-methylthiophenol is eliminated and the conjugated compound terthiophene is obtained.

Further precursor compounds which have been prepared in an analogous manner are 3,4-diethyl-2,5-di(2-thienyl)-tetrahydrothiophene and 3,4-di(tert-butyl)-2,5-di(2-thienyl)-tetrahydrothiophene. Thermal conversion proceeds under substantially identical conditions as mentioned above.

Further precursor compounds which can be prepared analogously are 3,4-bis((4-nitro)phenylthio)-2,5-di(2-thienyl)-tetrahydrothiophene and 3,4-bis(4-pyridyl)-2,5-di(2-thienyl)-tetrahydrothiophene.

Example 5

Synthesis of the dimer of 3,4-bis(phenylthio)-2,5-di(2-thienyl)-tetrahydrothiophene 3,4-bis(phenylthio)-2,5-di(5-bromo-2-thienyl)-tetrahydrothiophene To an ice-cooled solution of the unsymmetrical isomer of 3,4-bisuphenylthio)-2,5-di(2-thienyl)-tetrahydrothiophene as obtained in Example 2 (20.0 g, 42.8 mmol) in 80 ml DMF there is added in portions in about 5 minutes 20.5 g (115.2 mmol) N-bromosuccinimide (NBS). After part of the NBS had been added the temperature rose to 11° C. The addition of the remainder of the NBS was performed at 5–7° C. The mixture was stirred for 30 minutes, allowing the temperature to rise to 12° C. The solution is cooled and 4.0 g sodium dithionite is added. The mixture is stirred for 30 minutes at 5° C., then 30 minutes at 5 to 15° C. The mixture is cooled with ice and 50 ml water is added, followed by 50 ml toluene. After stirring for 5 minutes the mixture is poured in 300 ml water and 300 ml toluene. The layers are separated, the aqueous layer is extracted with 300 ml toluene, and the organic layers are washed with 2×100 ml water, then dried and rotary evaporated. The residue is filtered over a short aluminum oxide column using hexant/toluene (1/1) as the eluent. Rotary evaporation of the eluate, followed by crystallization of the residue from hexane/toluene affords 17.17 g of the unsymmetrical isomer of 3,4-bis(phenylthio)-2,5-di(5-bromo-2-thienyl)-tetrahydrothiophene (27.4 mmol, 64%).

$^1$H NMR (CDCl$_3$): δ3.9–4.2 (m, 2H), 4.95 (d, J=10 Hz, 1H), 5.4 (d, J=4 Hz, 1H), 6.8–6.9 (m, 4H), 7.0–7.3 (m, 10H). 3,4-bis(phenylthio)-2(5-bromo-2-thienyl)-5(5-tributylstannyl-2-thienyl)-tetrahydrothiophene A solution of 3,4-bis(phenylthio)-2,5-di(5-bromo-2-thienyl)-tetrahydrothiophene (6.26 g, 10.0 mmol) in 80 ml THF is cooled to at least −70° C. n-Butyllithium (5.0 ml, 12.5 mmol) in hexane is added in 2 minutes at these temperatures. The mixture is then stirred for 5 min at −80° C., after which tributyltin chloride (90%, 4.78 g, 14.7 mmol) in 5 ml THF is added over a 1 minutes period at −70° C. or less. The mixture is stirred for 30 min at −60 to −80° C., then allowed to warm up to −10° C. Water and hexane are added and the mixture is worked up in the usual way by pouring the mixture in water, extracting with hexane, washing with water, drying and rotary evaporating. The crude product is chromatographed over an aluminum oxide column (25×2 cm), using hexane containing increasing amounts of toluene as the eluent. Hexane elutes some impurities and the bistin compound, hexane containing some toluene elutes the product, hexane/toluene. (1/1) elutes some starting dibromide. The monotin compound weighs 6.05 g (7.24 mmol, 72%), it still contains some minor impurities.

dimer of 3,4-bis(phenylthio)-2,5-di(2-thienyl)-tetrahydrothiophene

A quantity of 6.05 g (7.24 mmol) of 3,4-bis(phenylthio)-2(5-bromo-2-thienyl)-5(5-tributylstannyl-2-thienyl)-tetrahydrothiophene, 5.66 g of 3,4-bis(phenylthio)-2,5-di(5-bromo-2-thienyl)-tetrahydrothiophene (9.04 mmol), dichlorobistriphenylphosphinepalladium (350 mg, 0.50 mmol) and 40 ml N,N-dimethylacetamide are heated for 48 hours at 65–70° C. Zinc powder (4.0 g) is added and the mixture is stirred for another 24 hours at 65–70° C. The solvent is removed under vacuum at 60° C., chloroform is added to the residue and the mixture is filtered over a short aluminum oxide column. The filtrate is rotary evaporated and the residue is chromatographed over an aluminum oxide column (20×3 cm) using hexane containing increasing amounts of toluene as the eluent. This gives several fractions which are rotary evaporated. The residue is dissolved in a small amount of toluene and this solution is then added, while stirring, to an excess of methanol. This causes precipitation of the products, which are subsequently analyzed by HPLC (Nucleosil 5NO$_2$ column, hexane/dichloromethane, 20/80 as the eluent, flow 0.5 ml/min). The monomer 3,4-bis(phenylthio)-2,5-di(2-thienyl)-tetrahydrothiophene has a retention time of 3.32 minutes, the dimer thereof a retention time of 5.29 minutes and the trimer thereof a retention time of 4.90 minutes. Two major fractions were obtained, 1.00 g dimer of 3,4-bis(phenylthio)-2,5-di(2-thienyl)-tetrahydrothiophene (almost pure) and 4.37 g dimer (containing 5–10% of the trimer).

The dimer and trimer of 3,4-bis(phenylthio)-2,5-di(2-thienyl)-tetrahydrothiophene are both precursor compounds having precursor units according to the formula (I), wherein X=S, $R_1$=$R_2$=phenyl, $R_3$=$R_4$=$R_5$=$R_6$=H, and showing excellent solubility in chloroform, dichloromethane, THF and the like. They can be suitably used in a method according to the invention. When heated at 200–250° C. for 15 minutes, thiophenol is quantitatively eliminated and a thiophene-containing conjugated compound, sexithiophene, is formed from the dimer, whereas from the trimer nonithiophene is formed.

Example 6

Synthesis of the trimer of 3,4-bis(phenylthio)-2,5-di(2-thienyl)-tetrahydrothiophene 3,4-bis(phenylthio)-2,5-di(5-tributylstannyl-2-thienyl)-tetrahydrothiophene A solution of 3,4-bis(phenylthio)-2,5-di(5-bromo-2-thienyl)-tetrahydrothiophene (7.96 g, 12.71 mmol) as obtained in Example 5, in 100 ml THF is cooled to a temperature below –80° C. n-Butyllithium (10.7 ml, 26.75 mmol) in hexane is added in 2 minutes at these temperatures. The mixture is then stirred for 5 minutes at –80° C. (longer stirring times lead to side-reactions, probably resulting from deprotonation at the 2-position of the tetrahydrothiophene ring), after which tributyltin chloride (90%, 10.7 g, 32.9 mmol) in 10 ml THF is added over a 3 min period at a temperature below –70° C. The mixture is stirred for 30 minutes at –60 to –80° C., then allowed to warm up to –25° C. Water and hexane are added and the mixture is worked up in the usual way. The crude product is chromatographed over an aluminum oxide column (30×4 cm), using hexane containing increasing amounts of toluene as the eluent. Hexane elutes some impurities, hexane containing a trace of toluene elutes the bistin compound, 3,4-bis(phenylthio)-2,5-di(5-tributylstannyl-2-thienyl)-tetrahydrothiophene, which still contains some minor impurities. The yield is 7.13 g (6.82 mmol, 54%).

trimer of 3,4-bis(phenylthio)-2,5-di(2-thienyl)-tetrahydrothiophene

The bistin compound (3.73 g, 3.57 mmol) obtained above, 3,4-bis(phenylthio)-2,5-di(5-bromo-2-thienyl)-tetrahydrothiophene (4.52 g, 7.22 mmol), the catalyst dichlorobistriphenylphosphinepalladium (315 mg, 0.45 mmol) and 25 ml N,N-dimethylacetamide are mixed and heated for 20 hours at 80° C. Another 100 mg catalyst (0.14 mmol) is added and the mixture is heated for 24 hours at 85° C. Zinc powder (2.0 g) is added and the mixture is stirred for 24 hours at 85° C. (Note: a lower temperature is beneficial, because some elimination of thiophenol is observed at 85° C.). The solvent is removed under vacuum, chloroform is added to the residue and the mixture is filtered over a short aluminum oxide column. The filtrate is rotary evaporated and the residue is chromatographed over an aluminum oxide column using hexane containing increasing amounts of toluene as the eluent. This gives several fractions which are rotary evaporated. The residue is dissolved in a small amount of toluene and this solution is then added, while stirring, to an excess of methanol. This causes precipitation of the products, which are subsequently analyzed by HPLC. The fractions consist of the dimer, dimer/trimer mixtures and almost pure trimer of 3,4-bis(phenylthio)-2,5-di(2-thienyl)-tetrahydrothiophene.

Example 7

The synthesis of 3,4-bis(phenylthio)-2,5-di[5-(2,2'-bithienyl)]-tetrahydrothiophene A 50 ml flask, equipped with condenser, magnetic stirrer and nitrogen inlet was charged with 56.2 mg (0.08 mmol) of di(triphenylphosphine)palladium(II)dichloride in 20 ml dry THF, followed by 500 mg (0.8 mmol) of the dibromo compound as obtained in Example 5 in 5 ml THF. Slowly, 670 mg (1.83 mmol) of 2-tributylstannylthiophene in 5 ml of THF was added under nitrogen. The synthesis of 2-tributylstannylthiophene is described by Kotani et al. in J. Organomet. Chem., 1992, 429, p403. The reaction mixture was stirred for 16 hours at 60° C. After cooling to room temperature, the THF was removed in vacuo, followed by the addition of 40 ml water with a few drops of HCl. The mixture was extracted three times with 20 ml ether. The combined organic phases were washed with water and saturated NaCl solution. The organic layer was dried with magnesium sulfate and removed in vacuo. The product, 3,4-bis(phenylthio)-2,5-di[5-(2,2'-bithienyl)]-tetrahydrothiophene, was purified by column chromatography using pentane: ethyl acetate [9:1] as eluent. Yield 203 mg (39.8%).

$^1$H NMR: δ=6.9–7.7 (m, 20H), 6.0 (d, 1H), 5.1 (d, 1H), 4.5 (q, 2H) ppm.

The product, 3,4-bis(phenylthio)-2,5-di[5-(2,2'-bithienyl)]-tetrahydrothiophene, is a precursor compound having a precursor unit according to the formula (I), wherein X=S, $R_1$=$R_2$=phenyl, $R_3$=$R_4$=$R_5$=$R_6$=H, which can be suitably used in a method according to the invention. Heating at 200–250° C. for 15 minutes results quantitatively in quinquethiophene.

Example 8

The synthesis of 3,4-bis(phenylthio)-2,5-di[5-(2,2':5',2''-terthienyl)]-tetrahydrothiophene

The synthesis of this tetrahydrothiophene is analogous to the synthesis described in Example 7, with this difference that 2-tributylstannylthiophene is replaced by 2-thienyl-5-tributylstannylthiophene, the synthesis of which is described by Hark et al. in Tetrahedron Lett., 1994, 35, p7719. The yield is 28.1%.

$^1$H NMR: δ=6.9–7.6 (m, 24 H), 6.0 (d, 1H), 5.1 (d, 1H), 4.5 (q, 2H) ppm.

The product, 3,4-bis(phenylthio)-2,5-di[5-(2,2':5',2''-terthienyl)]-tetrahydrothiophene, is a precursor compound having a precursor unit according to the formula (I), wherein X=S, $R_1$=$R_2$=phenyl, $R_3$=$R_4$=$R_5$=$R_6$=H, which can be suitably used in a method according to the invention. Heating at 200–250° C. for 15 minutes results quantitatively in septithiophene.

Example 9

The synthesis of the tetrahydrothiophene according to the formula:

The synthesis of this tetrahydrothiophene is analogous to the synthesis described in Example 7, with this difference that 2-tributylstannylthiophene is replaced by 2-(5-tributylstannyl-2-thienyl)-5-(2-thienyl)thiophene, which can be prepared in an analogous manner. The yield is 117 mg (86.3%).

$^1$H NMR: δ6.9–7.7 (m, 28 H), 6.0 (d, 1H), 5.1 (d, 1H), 4.5 (q, 2H) ppm.

The product is a precursor compound having a precursor unit according to the formula (I), wherein X=S, $R_1$=$R_2$=phenyl, $R_3$=$R_4$=$R_5$=$R_6$=H, which can be suitably used in a method according to the invention. Heating at 200–250° C. for 15 minutes results quantitatively in nonithiophene.

Example 10

Synthesis of poly[3,4-bis(phenylthio)-2,5-di(2-thienyl)-tetrahydrothiophene]

The dibromide 3,4-bis(phenylthio)-2,5-di(5-bromo-2-thienyl)-tetrahydrothiophene (0.5 g, 0.8 mmol), dissolved in 5 ml dimethylformamide, was added to a solution of 2,2'-bipyridyl (315 mg; 2.0 mmol) and Ni(cyclooctadiene)$_2$ (550 mg, 2.0 mmol) in 20 ml of dimethylformamide. The mixture was stirred for 24 hours at 60° C. under an inert atmosphere and precipitated into methanol (200 ml). The solid material was dissolved again in chloroform, washed with water, reprecipitated in ether and dried in vacuum overnight.

Yield: 245 mg (65.7%).

$^1$H NMR (DMSO) of the unsymmetrical polymer: δ4.3 (2H), 4.9 (1H), 5.85 (1H), 6.8–7.2 (16H).

The molecular weight of the precursor compound thus obtained is determined by gel permeation chromatography (GPC) as follows:

A solution of the polymer in chloroform (2 mg/ml) kept at a temperature of 40° C. is filtered over a 0.5 micron Millex filter and analysed on a GPC system, comprising a PL gel 5 mm Guard column connected in series to a second PL gel 5 mm Mixed C column and a UV/VIS detector set at 254 nm. The calibration is performed using polystyrene standards (Easical). The polymer elutes between 14 and 18 minutes with a maximum at 16 minutes. From the chromatograms, the number-average molecular weight of the polymer is calculated to be 3500, the weight-average molecular weight amounts to 6400 and the dispersion amounts to 1.8. By comparison, an almost pure sample of the trimer, which corresponds to the polymer with n=1, has a retention time of 19 minutes. From these data, the number-average molecular weight of the trimer is calculated to be 220, the weight-average molecular weight amounts to 230 and the dispersion amounts to 1.1. Theoretically, these numbers should equal 460, 460, and 1 respectively, which demonstrates that, as a person skilled in the art will expect, the GPC analysis of the polymer underestimates the molecular weight. In fact, the molecular weight appears to be underestimated by a factor of 2.

The product, poly[3,4-bis(phenylthio)-2,5-di(2-thienyl)-tetrahydrothiophene], is a precursor compound having precursor units according to the formula (I), wherein X=S, $R_1$=$R_2$=phenyl, $R_3$=$R_4$=$R_5$=$R_6$=H, which can be suitably used in a method according to the invention. It has excellent solubility in common organic solvents like chloroform, THF and dichloromethane. A thermogravimetric analysis (Perkin Elmer 7 Series Thermal Analysis System), whereby 1.538 mg of the polymer is heated at a rate 10° C. per min from 30 to 500° C., shows that phenylthiol is eliminated between approximately 190 and 270° C. thus forming the conjugated compound polythiophene.

Figure 1:
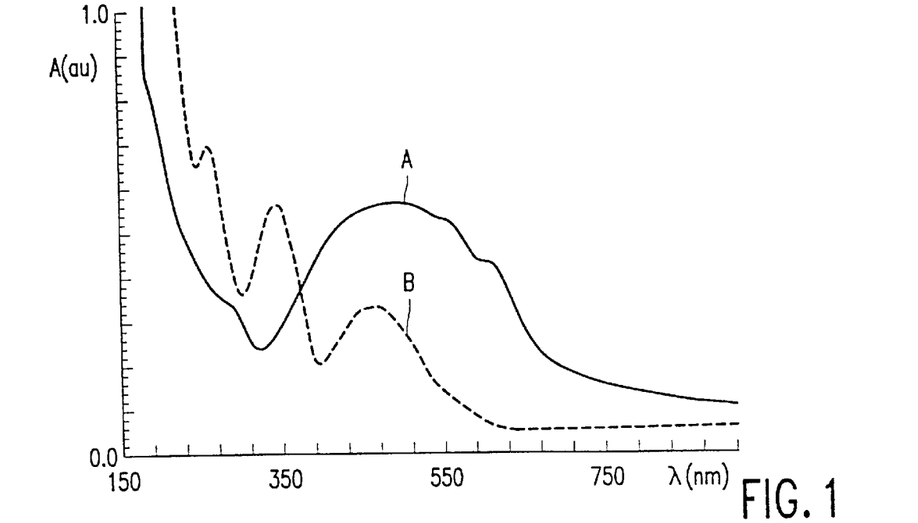
FIG. 1 shows the absorbance A (in arbitrary units au) as a function of wavelength λ (in nm) of a conjugated compound (curve A) prepared by the method according to the invention using a precursor compound (curve B) according to the invention.

FIG. 1 shows the absorbance A (in au) as a function of the wavelength λ (in nm) of a conjugated compound (curve A) prepared by the method according to the invention using a precursor compound (curve B) according to the invention. The spectra are recorded by means of a Perkin Elmer Lambda 9 spectrophotometer. The spectrum represented by curve B corresponds to the precursor compound poly[3,4-bis(phenylthio)-2,5-di(2-thienyl)-tetrahydrothiophene]. After evacuating for 2 hours at 250° C. and $10^{-5}$ Torr, the spectrum in curve A is obtained which shows a broad peak between 350 and 750 nm which is characteristic of polythiophene. However, unlike polythiophene samples which are not according to the invention, the broad peak shows various shoulders. This is considered to be due to the absence of topological defects.

Example 11

Using the polymer obtained in Example 10, a metal-insulator-semiconductor field-effect transistor (MISFET) is manufactured as follows:

A highly doped $n^{++}$-type silicon wafer which acts as the gate contact, is provided with a 200 nm insulating layer of thermally grown silicondioxide. Using standard lithographic techniques, a set of interdigitated source and drain gold contacts is provided on top of the insulator to give channel widths in the range of 3–20 mm and channel lengths in the range of 2–20 microns, thus rendering the MISFIT substrate complete. Source to drain resistances are in excess of $10^{12}$ Ohms. Subsequently, a 1 wt % solution of poly[3,4-bis (phenylthio)-2,5-di(2-thienyl)-tetrahydrothiophene] as prepared in Example 10 in chloroform is spincoated onto the MISFET substrate (3 seconds at 300 rpm followed by 30 s at 1000 rpm) to give a 50–150 nm thick precursor layer. The precise thickness is determined by means of a quartz substrate onto which the polymer is spincoated in an identical manner. The semiconducting layer is formed from the precursor layer by heating at a temperature of 250° C. at $10^{-5}$ Torr for 2 hours. The MISFET—in fact a set of MISFETS is formed—is now complete. A current voltage characteristic of a MISFET whose channel width is 10 mm and channel length is 5 microns is then determined by connecting a current measuring device and both the gate and drain to a voltage source. Starting at a gate bias $V_g$ of +20 V, the gate bias is swept to –20 V and back to +20 V. This is done at different drain voltages, the source being grounded at all times. In order to avoid doping of the semiconducting layer, samples are evacuated prior to measurement and the measurement itself is performed under nitrogen or vacuum. The result is shown in FIG. 2.

Figure 2:
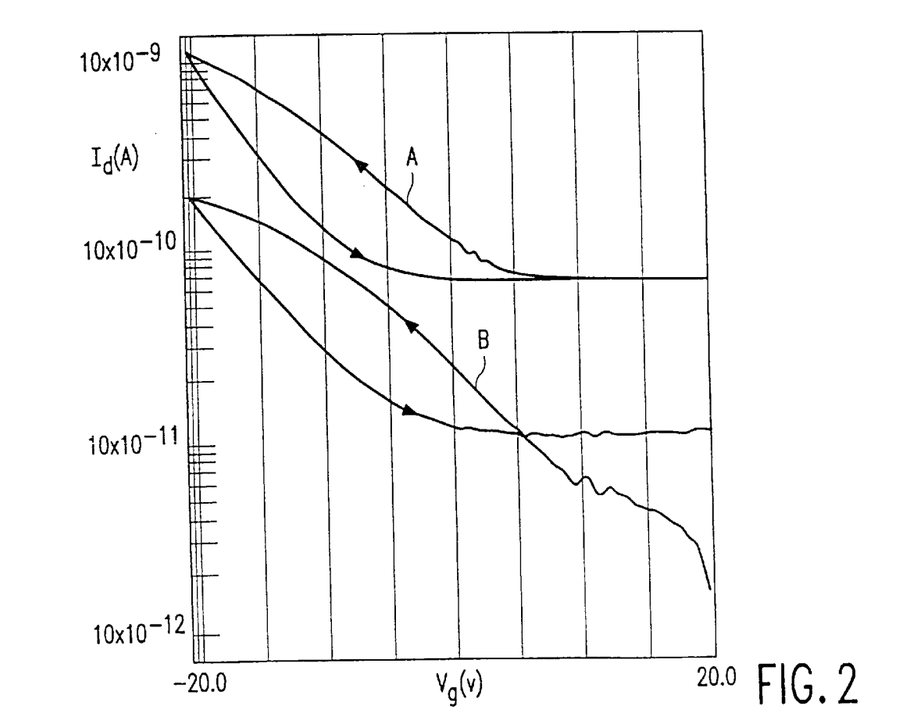
FIG. 2 shows the drain current $I_d$ (in A) as a function of the gate voltage $V_g$ (in V) at a drain voltage of −20 V (curve A) and −2 V (curve B) of a field-effect transistor according to the invention.

FIG. 2 shows the drain current $I_d$ (in A) as a function of the gate voltage $V_g$ (in V) at a drain voltage of –20 V (curve A) and –2 V (curve B) of a field-effect transistor according to the invention.

Using standard equations which model the current voltage characteristic of the MISFET taken at a drain voltage of –2 V, a voltage at which the MISFET is operating in the linear regime, the conductivity is calculated to be $8 \times 10^{-9}$ S/cm and the charge-carrier mobility is calculated to be $10^{-6}$ cm$^2$/(Vs).

Example 12

Example 11 is repeated with this difference that the polymer poly[3,4-bis(phenylthio)-2,5-di(2-thienyl)-tetrahydrothiophene] is (partially) replaced by either the dimer of 3,4-bis(phenylthio)-2,5-di(2-thienyl)-tetrahydrothiophene, which after conversion yields sexithiophene, the trimer of 3,4-bis(phenylthio)-2,5-di(2-thienyl)-tetrahydrothiophene, which after thermal conversion yields nonithiophene, or mixtures thereof. Some typical values of the conductivity ρ and charge-carrier mobility μ are collected in Table 1.

TABLE 1

| polymer (wt %) | dimer (wt %) | trimer (wt %) | ρ (S/cm) | $\mu$(cm$^2$/(V$_s$)) |
|---|---|---|---|---|
| 0 | 100 | 0 | $2 \times 10^{-8}$ | $1 \times 10^{-5}$ |
| 0 | 0 | 100 | $5 \times 10^{-7}$ | $6 \times 10^{-5}$ |
| 50 | 50 | 0 | $6 \times 10^{-6}$ | $5 \times 10^{-4}$ |
| 25 | 0 | 75 | $9.5 \times 10^{-7}$ | $2.5 \times 10^{-4}$ |

From the results in this table it is apparent that the most favourable electrical properties are obtained, a low conductivity in combination with a high mobility being particularly desirable, if mixtures of polymers and oligomers of thiophene are used.

What is claimed is:

1. A semiconductor device having a semiconducting layer comprising a polythiophene which is derived by thermal separation of thermally separable substituents from a soluble precursor compound having a precursor unit consisting of a tetrahydrothiophene or tetrahydrofuran unit having thermally separable substituents —SR$_1$ and —SR$_2$ groups, wherein R$_1$ are R$_2$ are independently selected from alkyl and aryl groups.

2. A semiconductor device as claimed in claim 1, wherein said precursor unit is selected from compounds having the formula (I)

(I)

wherein X is equal to O or S; R$_1$ and R$_2$ are independently selected as an alkyl or aryl group; R$_3$ and R$_4$ are methyl, ethyl, methoxy, ethoxy, nitro or hydrogen; and R$_5$ and R$_6$ are hydrogen.

3. A semiconductor device as claimed in claim 2, wherein R$_1$ and R$_2$ of the precursor unit are an alkyl or aryl group selected from the group consisting of phenyl, 4-methylphenyl, 4-chlorophenyl, 4-nitrophenyl, 4-pyridyl, ethyl, and tert-butyl groups.

4. A semiconductor device as claimed in claim 2, wherein said precursor unit is a 2,5-dithienyltetrahydrothiophene or 2,5-dithienyltetrahydrofuran unit.

5. A semiconductor device as claimed in claim 2, wherein said precursor unit is a 3-phenylthio-2,5-di(2-thienyl)-2,3-dihydrohydrothiophene unit.

6. A semiconductor device as claimed in claim 1, wherein said soluble precursor compound is selected from the group consisting of 3,4-bis(phenylthio)-2,5-di(2-thienyl)-tetrahydrofuran, 3,4-bis(phenylthio)-2,5-di(2-thienyl)-tetrahydrothiophene, 3,4-bis((4-chloro)phenylthio)-2,5-di (2-thienyl)-tetrahydrothiophene, 3,4-bis((4-methyl) phenylthio)-2,5-di(2-thienyl)-tetrahydrothiophene, 3,4-diethyl-2,5-di(2-thienyl)-tetrahydrothiophene, 3,4-di(tert-butyl)-2,5-di(2-thienyl)-tetrahydrothiophene, 3,4-bis((4- nitro)phenylthio)-2,5-di(2-thienyl)-tetrahydrothiophene, 3,4-bis((4-pyridyl)-2,5-di(2-thienyl)-tetrahydrothiophene, 3,4-bis(phenylthio)-2,5-di(5-bromo-2-thienyl)-tetrahydrothiophene, dimer of 3,4-bis(phenylthio)-2,5-di(2-thienyl)-tetrahydrothiophene, trimer of 3,4-bis(phenylthio)-2,5-di(2-thienyl)-tetrahydrothiophene, 3,4-bis(phenylthio)-2,5-di[5-(2,2'-bithienyl)]-tetrahydrothiophene, 3,4-bis(phenylthio)-2,5-di[5-( 2,2':5',2"-terthienyl)]-tetrahydrothiophene, and poly[3,4-bis(phenylthio)-2,5-di(2-thienyl)-tetrahydrothiophene].

7. A semiconductor device as claimed in claim 6 wherein said precursor compound is 3,4-bis(phenylthio)-2,5-di(2-thienyl)-tetrahydrofuran.

8. A semiconductor device as claimed in claim 6 wherein the soluble precursor compound is 3,4-bis(phenylthio)-2,5-di(2-thienyl)-tetrahydrothiophene.

9. A semiconductor device as claimed in claim 6, wherein the soluble precursor compound is 3,4-bis((4-chloro)phenylthio)-2,5-di(2-thienyl)-tetrahydrothiophene.

10. A semiconductor device as claimed in claim 6, wherein the soluble precursor compound is 3,4-bis((4-methyl)phenylthio)-2,5-di(2-thienyl)-tetrahydrothiophene.

11. A semiconductor device as claimed in claim 6, wherein the soluble precursor compound is 3,4-diethyl-2,5-di(2-thienyl)-tetrahydrothiophene.

12. A semiconductor device as claimed in claim 6, by wherein the soluble precursor compound is 3,4-di(tert-butyl)-2,5-di(2-thienyl)-tetrahydrothiophene.

13. A semiconductor device as claimed in claim 6, wherein the soluble precursor compound is 3,4-bis((4-nitro)phenylthio)-2,5-di(2-thienyl)-tetrahydrothiophene.

14. A semiconductor device as claimed in claim 6, wherein the soluble precursor compound is 3,4-bis((4-pyridyl)-2,5-di(2-thienyl)-tetrahydrothiophene.

15. A semiconductor device as claimed in claim 6, wherein the soluble precursor compound is 3,4-bis(phenylthio)-2,5-di(5-bromo-2-thienyl)-tetrahydrothiophene.

16. A semiconductor device as claimed in claim 6, wherein the soluble precursor compound is the dimer of 3,4-bis(phenylthio)-2,5-di(2-thienyl)-tetrahydrothiophene.

17. A semiconductor device as claimed in claim 6, wherein the soluble precursor compound is the trimer of 3,4-bis(phenylthio)-2,5-di(2-thienyl)-tetrahydrothiophene.

18. A semiconductor device as claimed in claim 6, wherein the soluble precursor compound is 3,4-bis(phenylthio)-2,5-di[5-(2,2'-bithienyl)]-tetrahydrothiophene.

19. A semiconductor device as claimed in claim 6, wherein the soluble precursor compound is 3,4-bis(phenylthio)-2,5-di[5-(2,2':5',2"-terthienyl)]-tetrahydrothiophene.

20. A semiconductor device as claimed in claim 6, wherein the soluble precursor compound is poly[3,4-bis(phenylthio)-2,5-di(2-thienyl)-tetrahydrothiophene].

* * * * *